United States Patent
Rahman (10) Patent No.: US 11,974,735 B2
(45) Date of Patent: May 7, 2024

(54) METHOD AND APPARATUS FOR PERCUTANEOUS SURGICAL OPERATIONS

(71) Applicant: Ra'Kerry Rahman MD PA, Houston, TX (US)

(72) Inventor: Ra'Kerry Kahlil Rahman, Houston, TX (US)

(73) Assignee: Ra'Kerry Rahman, Houston, TX (US)

( * ) Notice: Subject to any disclaimer, the term of this patent is extended or adjusted under 35 U.S.C. 154(b) by 0 days.

(21) Appl. No.: 17/945,838

(22) Filed: Sep. 15, 2022

(65) Prior Publication Data
US 2024/0090885 A1     Mar. 21, 2024

(51) Int. Cl.
*A61B 17/02* (2006.01)
*A61B 17/00* (2006.01)

(52) U.S. Cl.
CPC ............. *A61B 17/0218* (2013.01); *A61B 2017/00022* (2013.01)

(58) Field of Classification Search
CPC ................ A61B 17/0218; A61B 2017/000222
USPC ............... 600/201–245; 606/201–245
See application file for complete search history.

(56) References Cited

U.S. PATENT DOCUMENTS

| | | | |
|---|---|---|---|
| 2010/0331883 A1* | 12/2010 | Schmitz | A61B 17/320758 606/279 |
| 2011/0190588 A1* | 8/2011 | McKay | A61B 17/0206 600/202 |
| 2013/0237766 A1* | 9/2013 | Pell | A61B 5/0051 600/211 |
| 2018/0116489 A1* | 5/2018 | Aferzon | A61B 1/0607 |
| 2020/0015925 A1* | 1/2020 | Scheib | A61B 1/00043 |

FOREIGN PATENT DOCUMENTS

WO    WO-2010123825 A1 * 10/2010    ............... A61B 1/32

* cited by examiner

*Primary Examiner* — Eduardo C Robert
*Assistant Examiner* — Tara Rose E Carter
(74) *Attorney, Agent, or Firm* — EWING & JONES, PLLC (57) ABSTRACT

Aspects of the disclosure provide a method and apparatus for retraction of body structures during spinal surgery as well as identification of nerve structures through use of a piezoelectric device.

16 Claims, 6 Drawing Sheets

METHOD AND APPARATUS FOR PERCUTANEOUS SURGICAL OPERATIONS

CROSS-REFERENCE TO RELATED APPLICATIONS

None.

FIELD OF THE DISCLOSURE

Aspects of the disclosure relate to apparatus and methods for surgery. More specifically, aspects of the disclosure relate to apparatus and methods for spine surgery that use a minimized incision size of the surgery to minimize bodily damage resulting from the surgery. Moreover, during such surgery, aspects of the disclosure relate to methods of retraction and identification of body structures during surgical procedures.

BACKGROUND

Spinal surgery is a complicated specialty where specially trained physicians can encounter various difficult problems. Spinal surgery is made especially difficult by the number of nerves and other structures that are placed in close proximity to the spine. Patients often seek redress of pain and movement restriction caused by such pain through spinal surgery. The decision to undergo surgery, however, is not made lightly by patients as spine surgery can carry significant risk to the patient. Such risks include further restriction of movement, pain and various deterioration conditions.

In general, spinal surgery often seeks to either provide a supporting structure near the spine or to remove various bone or soft tissues that are problematic. As a non-limiting example, placement of a supporting structure near a person's spine can aid in structural support for the individual. This aid in structural support allows for a transfer of structural loading from the spine to the newly added support structure. Reduced forces on the spine, as well as areas near the spine, helps decompress nerves that may be under tension or compression. This decompression is often felt by patients as a reduction of pain as the nerves are no longer under such structural forces.

Placement of structural bracing systems around the spine is not an easy task for even the most skilled of physicians. To this end, surgeons operate in areas that are generally devoid of interfering bodily structures in order to limit patient discomfort and limit potential complications. In the early 1970's, research was conducted on the most advantageous place to conduct spinal surgery, and an area in the shape of a triangle, near the spine, was identified as the best possible location for surgery. This area is mostly devoid of vascular and neural structures of significant importance. Known as "Kambin's triangle", this area, while generally known, can vary from patient to patient. As time has progressed, doctors have more accurately described the "triangle" as a "prism", as further research and development have identified the area more precisely. Despite this continuing research, there are still variations from patient to patient where more vital nerves and structures may be "pushed" into the areas previously thought to be clear for surgery. Several things can occur to a patient in order for these structures to impinge on Kambin's triangle. As a non-limiting example, a patient may have scar tissue near the spine that effectively pushes nerves into the "triangle" or "prism" that should be clear of such structures. As a result, doctors cannot operate with impunity in Kambin's triangle as many patients have such intrusions into this area. As will be understood, each patient is unique, causing the doctor to be mindful during operations.

Surgery in these areas, therefore, can take long periods of time compared to other areas of the body. As the surgeon may have little to no idea of the state of underlying structures, there is a need to provide a method and apparatus that will help identify structures during surgical operations.

There is a further need to provide methods and apparatus that will help in minimizing the amount of incision near the spine, reducing the amount of damage to a patient.

There is a still further need to provide a method of retraction of tissue that can allow a surgeon to access areas around the spine from the minimized incision.

There is also a need to provide the retraction method such that retraction is conducted safely and expeditiously as well as flexibly, wherein larger retraction is possible if a larger volume is necessary for the attending physician.

There is also a further need to allow for a physician to gain access to spinal areas to allow for placement of robust structural reinforcements around the spine, allowing patients the ability to have structural spinal support.

There is also a need to provide for use of basic structural support around the spine as compared to more elaborate and expensive smaller supports that may not be as beneficial to a patient compared to a more robust support.

There is a need to provide an apparatus and methods that are easier to operate than conventional apparatus and methods.

There is a further need to provide apparatus and methods that do not have the drawbacks discussed above.

There is a still further need to reduce economic costs associated with operations and apparatus described above with conventional tools.

SUMMARY

So that the manner in which the above recited features of the present disclosure can be understood in detail, a more particular description of the disclosure, briefly summarized below, may be had by reference to embodiments, some of which are illustrated in the drawings. It is to be noted that the drawings illustrate only typical embodiments of this disclosure and are therefore not to be considered limiting of its scope, for the disclosure may admit to other equally effective embodiments without specific recitation. Accordingly, the following summary provides just a few aspects of the description and should not be used to limit the described embodiments to a single concept.

In one example embodiment, a method is disclosed. The method comprises inserting a multi-zone piezoelectric apparatus into a surgical site and generating a signal for actuation of at least one piezoelectric component. The method further comprises receiving the signal for action at the multi-zone piezoelectric apparatus. The method further comprises processing the signal by the multi-zone piezoelectric apparatus. The method may further comprise activating at least one piezoelectric component of the piezoelectric apparatus. The method may further comprise reflecting the signal back to the apparatus from at least one structure. The method may also provide for receiving the reflected signal by the apparatus. The method may also provide for analyzing the reflected signal and indicating a type of structure encountered by the signal.

In one example embodiment, an apparatus for retraction is disclosed. The apparatus comprises a fixated portion and a movable portion, wherein the movable portion is configured to move relative to the fixated portion upon an actuation. The apparatus is further configured with an actuator configured to receive a signal, process the received signal and perform an actuation to move the movable portion relative to the fixated portion.

In another embodiment, a method is described. The method comprises placing a retraction device within an opening, the retraction having both a fixed portion and an expandable portion. The method further comprises generating a signal for actuation of the retraction device. The method further comprises receiving the signal is received at the retraction device. The method further comprises processing the signal at the retraction device to determine when an actuation is to occur. The method further comprises actuating an actuator when the processing of the signal is determined that an actuation is to occur. The method further comprises moving the expandable portion through the actuator.

BRIEF DESCRIPTION OF THE DRAWINGS

So that the manner in which the above recited features of the present disclosure can be understood in detail, a more particular description of the disclosure, briefly summarized above, may be had by reference to embodiments, some of which are illustrated in the drawings. It is to be noted, however, that the appended drawings illustrate only typical embodiments of this disclosure and are therefore not be considered limiting of its scope, for the disclosure may admit to other equally effective embodiments.

To facilitate understanding, identical reference numerals have been used, where possible, to designate identical elements that are common to the figures ("FIGS."). It is contemplated that elements disclosed in one embodiment may be beneficially utilized on other embodiments without specific recitation.

DETAILED DESCRIPTION

In the following, reference is made to embodiments of the disclosure. It should be understood, however, that the disclosure is not limited to specific described embodiments. Instead, any combination of the following features and elements, whether related to different embodiments or not, is contemplated to implement and practice the disclosure. Furthermore, although embodiments of the disclosure may achieve advantages over other possible solutions and/or over the prior art, whether or not a particular advantage is achieved by a given embodiment is not limiting of the disclosure. Thus, the following aspects, features, embodiments and advantages are merely illustrative and are not considered elements or limitations of the claims except where explicitly recited in a claim. Likewise, reference to "the disclosure" shall not be construed as a generalization of inventive subject matter disclosed herein and should not be considered to be an element or limitation of the claims except where explicitly recited in a claim.

Although the terms first, second, third, etc., may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first", "second" and other numerical terms, when used herein, do not imply a sequence or order unless clearly indicated by the context. Thus, a first element, component, region, layer or section discussed herein could be termed a second element, component, region, layer or section without departing from the teachings of the example embodiments.

When an element or layer is referred to as being "on," "engaged to," "connected to," or "coupled to" another element or layer, it may be directly on, engaged, connected, coupled to the other element or layer, or interleaving elements or layers may be present. In contrast, when an element is referred to as being "directly on," "directly engaged to," "directly connected to," or "directly coupled to" another element or layer, there may be no interleaving elements or layers present. Other words used to describe the relationship between elements should be interpreted in a like fashion. As used herein, the term "and/or" includes any and all combinations of one or more of the associated listed terms.

Some embodiments will now be described with reference to the figures. Like elements in the various figures will be referenced with like numbers for consistency. In the following description, numerous details are set forth to provide an understanding of various embodiments and/or features. It will be understood, however, by those skilled in the art, that some embodiments may be practiced without many of these details, and that numerous variations or modifications from the described embodiments are possible. As used herein, the terms "above" and "below", "up" and "down", "upper" and "lower", "upwardly" and "downwardly", and other like terms indicating relative positions above or below a given point are used in this description to more clearly describe certain embodiments.

As will be understood, the aspects disclosed above provide methods and apparatus that help in minimizing the amount of incision near the spine, reducing the amount of damage to a patient.

The aspects disclosed above also provide an apparatus and a method of retraction of tissue that can allow a surgeon to access areas around the spine from the minimized incision.

The apparatus and methods described also provide a retraction method such that retraction is conducted safely and expeditiously as well as flexibly, wherein larger retraction is possible if a larger volume is necessary for the attending physician.

The apparatus and methods described above also allow for a physician to gain access to spinal areas to allow for placement of robust structural reinforcements around the spine, allowing patients the ability to have structural spinal support.

The aspects described also provide for use of basic structural support around the spine as compared to more elaborate and expensive smaller supports that may not be as beneficial to a patient compared to a more robust support.

Aspects of the disclosure also allow for the surgeon to identify sensitive structures, such as nerves, during surgery in order to avoid these structures.

Figure 1:
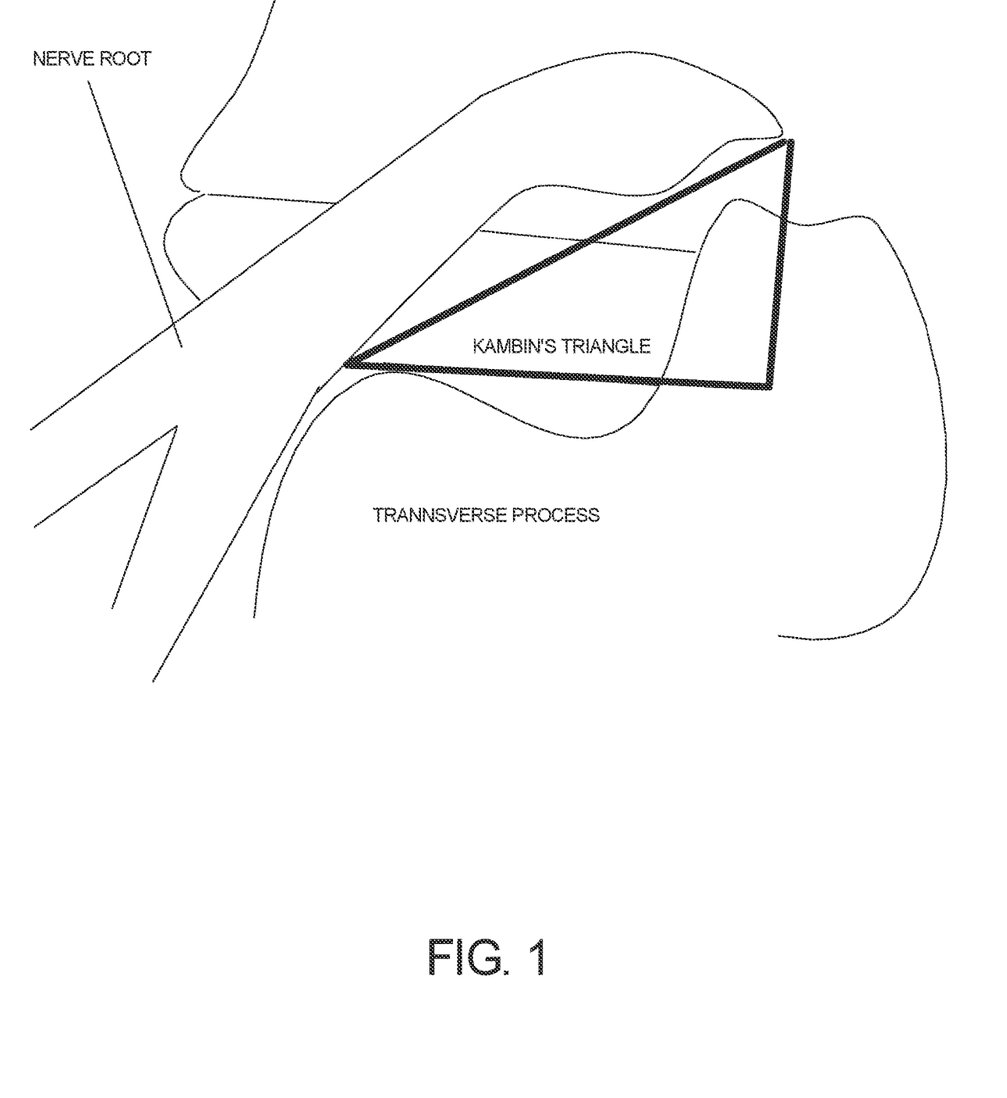
FIG. 1 is a diagram of Kambin's triangle in a hypothetical patient.

Referring to FIG. 1, an area of a hypothetical patient is illustrated. The area is in the vicinity of a person's spine that is regularly used to make incisions during surgical procedures. The area, known as Kambin's triangle 100 is an anatomical corridor that may be used to access critical structures, such as nerves and the spine, in a vast variety of spinal procedures. Kambin's triangle 100 is often used as a starting point for surgical procedures as there are less vascular and neural structures in the area. The size of Kambin's triangle 100 varies according to each patient, and the size has been in debate among medical practitioners for some time. As can been seen in FIG. 1, an existing nerve 102 has a nerve root 104 that enters the spinal column 106. It is desired to conduct medical procedures without impacting the nerve 102 of the nerve root 104 during the procedure. If, for example, damage to the local area of a patient occurs, the nerve 102 and a portion of the nerve root 104, if it is not severed, can slide/move in three dimensional space, thereby either increasing or, in the case of more complicated cases, decreasing the amount of space within Kambin's triangle 100.

In cases of severe trauma or deterioration, the available space within Kambin's triangle 100 can be quite limited. In conventional surgery, a physician cannot be certain of the position of the nerve 102 or the nerve root 104. Thus, the nerve 102 or nerve root 104 may be impacted by the procedure, with deleterious consequences.

These types of scenarios, however, are avoided with the methods and apparatus of the current disclosure. As the nerve root 104 is generally fixed at the spinal column 106, a surgeon can at least identify a starting point for an incision that will allow for reduced risk of impacting the nerve 102 or nerve root 104 during the incision. Aspects of the disclosure allow for an apparatus, described in FIG. 2, to be inserted within the initial incision that will allow for a variable size retraction for the attending physician. Such a variable size retraction allows the physician to gently move the nerve 102 to the side, allowing access to spinal column 106.

In aspects of the disclosure, the apparatus used for variable retraction allows a physician to maximize the amount of open volume in a patient without causing permanent damage. This increased volume can be used to great benefit of the patient. In one non-limiting embodiment, since the retraction allows a maximum of volume to be exposed, a patent may have a larger implanted structure placed around the spine. In a non-limiting embodiment, a patient with a degenerative condition may require extra structural support be placed in a vicinity of the spine. In this instance, the patient may have difficulty with pain in the area due to stress being placed on the nerve 102 or nerve root 104. The stress is due to structural loading occurring at either the nerve 102, nerve root 104 or other accompanying and closely related structures. In order to reduce the amount of stress that a patient will experience, an arrangement may be implanted into the retracted volume and supported by the bone structure of the spinal column 106. During the operation, for example, the arrangement is fixated to the spinal column 106 when the patient is in a position that removes structural stress in that area. Fixation of the arrangement allows for transfer of structural forces to other areas of the spinal column 106, thereby creating an area where the nerve 102 and nerve root 104 would have a reduced structural load. Such a reduced structural load minimizes deterioration in the affected area and ultimately decreases pain to a patient.

In embodiments, as described above, the implanted arrangement may be maximized in overall size for the patient. Such maximized sized implanted arrangements are more cost effective for patients than smaller and more delicate arrangements. In this way, a patient may incur the benefits of using a maximized sized implant from a structural standpoint, while maintaining the overall economic benefit of a more reasonably priced implant. Moreover, as larger implants may be used, the delicate procedures of installing smaller and more complicated implants are avoided. As less time is used for such implant procedures, the economics of such a procedure are also greatly enhanced as less surgical room time is used.

Figure 2:
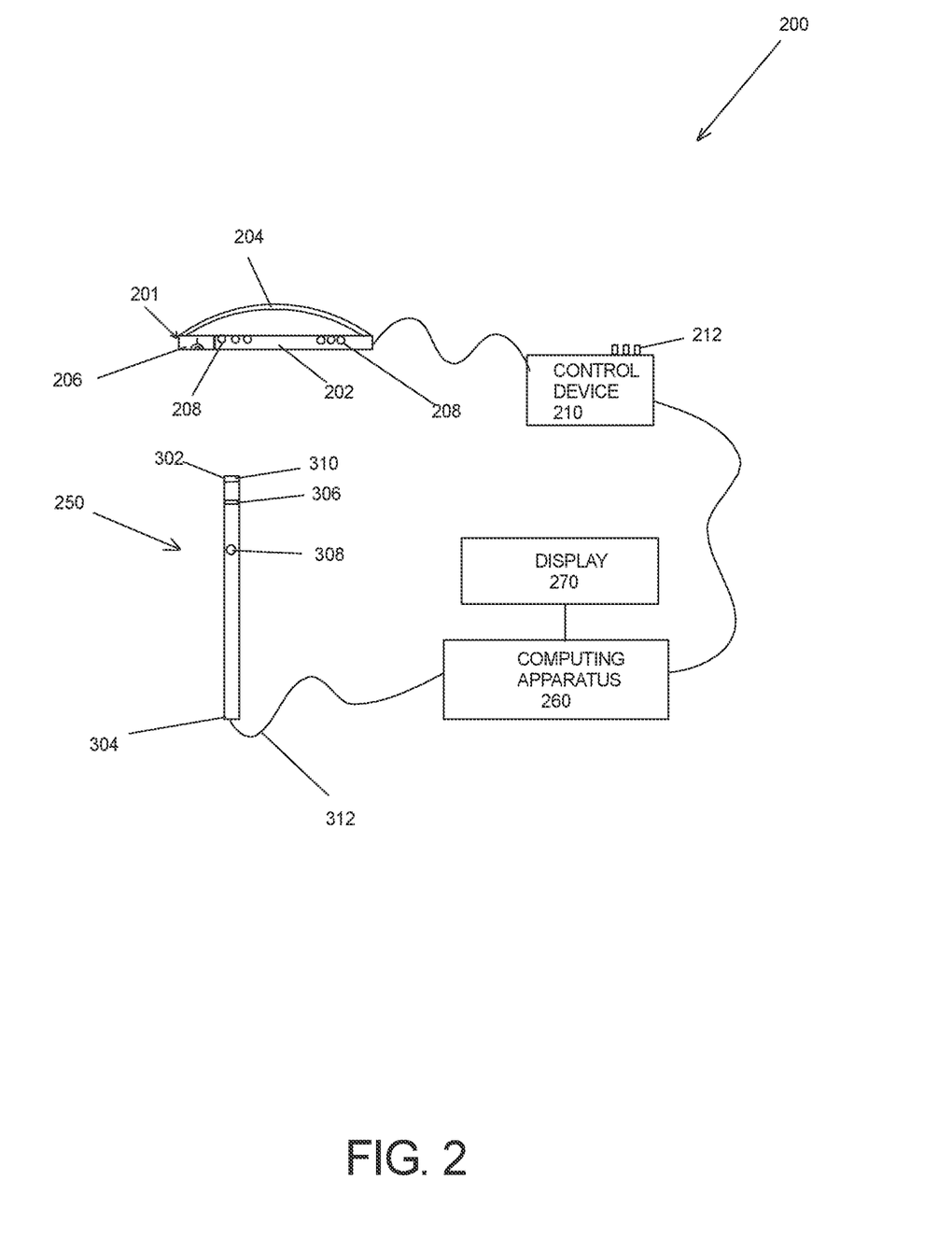
FIG. 2 is a cross-section of an apparatus in accordance with one example embodiment of the disclosure, wherein the apparatus has a retraction device and a nerve identification device used in spinal surgery.
Figure 4:
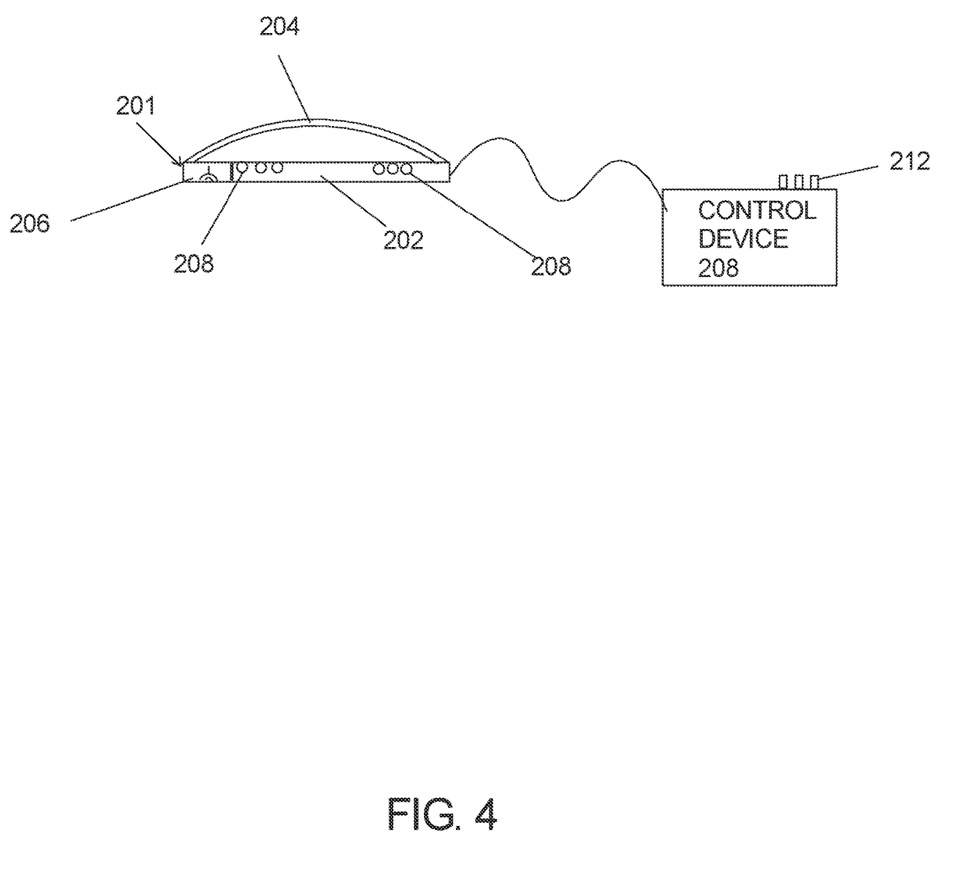
FIG. 4 is a perspective view of the apparatus of FIG. 2, in one example embodiment of the disclosure.

Referring to FIGS. 2 and 4, a surgical apparatus 200 used for surgical operations is illustrated. As described, non-limiting applications of the surgical apparatus 200 include for procedures at or near the spine of a patient and retraction, as described above. The surgical apparatus 200 may include a retraction device 201. The retraction device 201 has a fixated portion 202 and a movable portion 204. In one embodiment, the fixated portion 202 has a flat side that is not deformable. Other configurations are possible, wherein the fixated portion 202 has a rounded or curved shape. The moveable portion 204 allows for variable expansion, based upon a surgeon's initiation of movement. The retraction device 201 may have different configurations to allow the surgeon to make an incision that is small and allow for the insertion of the retraction device 201 into the body. In one example embodiment, the moveable portion 204 is moved in relation to the fixated portion 202 through an actuator 206. The actuator 206 may be a manual device that the surgeon may control to open the moveable portion 204 relative to the fixated portion 202. The actuator 206 may be a manually operated unit, in one embodiment. The actuator 206 may also be an electromechanically operated unit for movement of the moveable portion 204 relative to the fixated portion 202. In either the manual embodiment or the electromechanically operated embodiment, the movement may be controlled precisely by the surgeon to expand or contract a desired amount. Either separately or incorporated into the retraction device 201, an illumination device 208 may be provided for illumination of the incision. Different levels of illumination may be provided by the illumination device 208. For example, the illumination device 208 may have an arrangement of light emitting diodes ("LEDs") that illuminate when powered. The illumination device 208 may be controlled such that a smaller or larger amounts of LEDs are illuminated, therefore decreasing or increasing the amount of illumination. The illumination device 208 may be controlled by a control device 210 that initiates power or stops power from being delivered to the LED's. The control device 210 may also provide predefined selections 212 of the amount of illumination.

In embodiments, the retraction device 201 has components that may be cleaned for multiple reuse. Components may be surface coated or constructed from stainless steel such that they may be sanitized before use with another patient. Conventional retractors used in spinal surgery may be simple type split tong devices, known as Meyerding retraction devices. Other retraction devices used in conventional surgery include devices shaped as L shaped devices. Such devices are difficult to use by the surgeon as incision sizes are reduced, therefore the retraction device 201 has significant benefits.

In embodiments, the retraction device 201 may be a screw-driven unit. For precise opening control, the screw threading used may be fine, therefore allowing of very precise retraction capabilities. In other embodiments, the retraction device 201 may be operated through a hydraulic system. In still other embodiments, the retraction device 201 may be pneumatically controlled. As will be understood, in the instance of a retraction device 201 that uses a hydraulic system or pneumatic system, safety systems may be used such that inadvertent loss of power will not affect the retracted area. In both hydraulic and pneumatic control, for example, an accumulator reservoir may be used to maintain pressure and maintain retraction capabilities. Also in such instances, a safety valve may be used to bleed pressure from the accumulator reservoir, thereby allowing closure of the retraction device 201 for removal from the incision. In all embodiments, redundant systems may be provided such that a single failure of a component will not affect the retraction capability of the retraction device 201.

In one non-limiting embodiment, the actuator 206, may be operated through a wired connection. In other embodiments, the actuator 206 may be wirelessly controlled. Known wireless technologies, such as Bluetooth and WiFi connections may be used.

Figure 3:
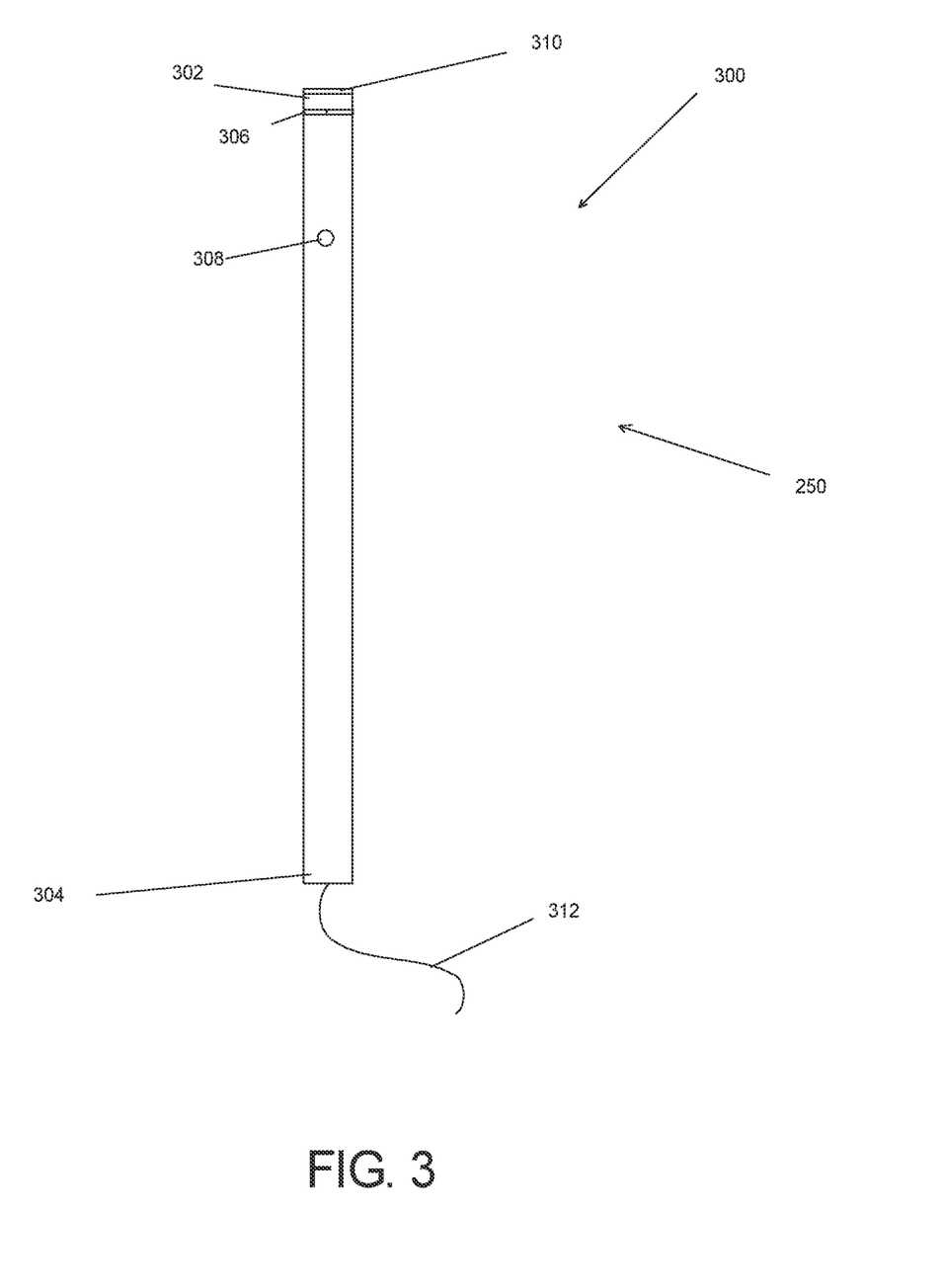
FIG. 3 is a side view of a nerve identification device using a piezoelectric apparatus used in spinal surgery.

The surgical apparatus 200 may also be configured with a nerve detection device 250. In order to identify a nerve, the nerve detection device 250 is configured with a tip arrangement 310 and a side arrangement 306. In one example embodiment, the nerve detection device 250 may use optical characterization of tissue to determine the presence of nerves. In one example embodiment, in-vivo measurements are made of tissue, during surgery, to allow for identification of nerve tissue. Such measurements are not performed in conventional apparatus. Optical measurements may include the use of diffuse reflectance spectroscopy. In such embodiments, light produced in a range of 400-1600 nm may be used. Reflected light from the tissue may be measured through a sensor placed in the tip arrangement 310 and/or the side arrangement 306 and compared to spectroscopy samples of different types of tissue, such as fat, ligament, nerve and bone as non-limiting embodiments. The surgeon, therefore, can identify the presence of different structures during operation. The variability of Kambin's triangle, therefore can be minimized for the patient, resulting in an overall less risky surgical procedure.

In other embodiments, the nerve detection device 250 may be configured with piezoelectric circuitry in the tip arrangement 310 and the side arrangement 306. Such piezoelectric circuitry may be used to activate materials within the incision. According to the vibrational dynamics of the materials activated by the piezoelectric circuitry, a surgeon is enabled to determine the type of materials at/near the tip arrangement 310 as well as at/near the side arrangement 306 of the nerve detection device 250. As will be understood, various implementations are possible where more tip arrangements 310 and side arrangements 306 are positioned. Each of the tip arrangements 310 and side arrangements 306 may be individually controlled and monitored. A computing apparatus 260 may receive data from the tip arrangements 310 and the side arrangements 306. Analysis may be performed within the computing apparatus 260 for identification of the type of body structure encountered. In one implementation, a display 270 may be provided to allow the surgeon to identify the type of structure being encountered. In embodiments, video capture, processing and display may be provided to allow for magnification of the areas undergoing surgery.

Referring to FIG. 3, the nerve detection device 250 is further illustrated. The nerve detection device 250 is provided with a body 300 that has a first end 302 and a second end 304. The body 300 is in a configuration of a tube, to allow a passage of materials through the tube. In non-limiting embodiments, the body 300 may be solid, such that the surgeon touches portions of materials within the incision to determine the presence differing structures. In other embodiments, the body is configured as a tube, allowing for instrumentation, medical instruments and/or medical components to be placed through the body 300. The nerve detection device 250 is configured with an indicator 308 that may illuminate different colors indicating the type of structure being encountered. At the first end 302, a tip arrangement 310 is positioned to send and receive signals into and from a patient. Another set of side arrangements 306 may be located on the sides of the nerve detection device 250 to allow the surgeon to identify structures to the side of the nerve detection device 250. The nerve detection device 250 may be configured as a tube, in a non-limiting embodiment. Electronics, such as the indicator 308 and piezoelectric transducers in the tip arrangement 310 and the side arrangement 306 may be connected to computer and electrical inputs through wiring 312.

Figure 5:
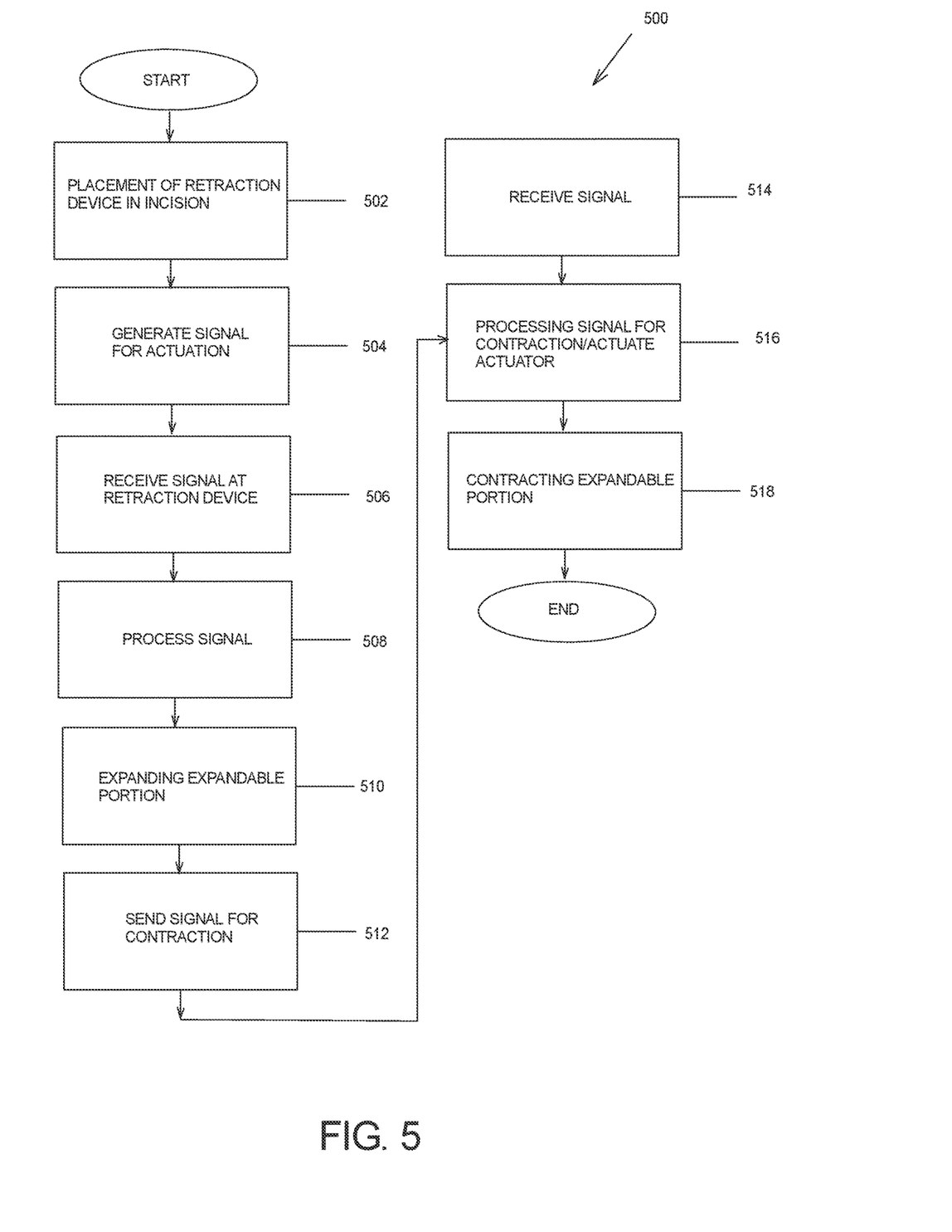
FIG. 5 is a method for retraction of materials during a spinal surgery, wherein a deformable system is used.

The apparatus aspects described may be configured such that a method for percutaneous spinal surgery may be accomplished. The method, described in FIG. 5, may be accomplished by the apparatus described in FIG. 2, as a non-limiting embodiment. Referring to FIG. 5, a first method 500 for retraction in a spinal surgery is disclosed. The first 310 method 500 includes, at 502, placing a retraction device within an opening, the retraction having both a fixed portion and an expandable portion. The opening may be created by a surgeon, for exploratory and/or corrective medical procedures. In non-limiting embodiments, the placement of a device to aid in structural support of a patient's spine may be performed. In other embodiments, spinal surgery for fixating two vertebrae together may be performed. At 504, a signal for actuation of the retraction device is generated. The generation of the signal may be, for example, initiated by a surgeon through interface with an input device. The input device may be through a computer, a foot pedal or a switch in non-limiting embodiments. At 506, the signal is received at the retraction device. The sending of the signal may be through a wired connection between the signal generator or through a wireless connection. At 508, the signal is processed by the retraction device such that an actuator is actuated. At 510, the expandable portion of the retraction device is expanded compared to the fixed portion, thereby causing an enlargement of the opening. The enlargement of the opening through the expandable portion moving related to the fixed or fixated portion may be caused through a mechanical screw action in one embodiment. In other embodiments, the movement may be caused through a pneumatic action or hydraulic action. The method may also comprise, at 512, sending a signal for compression/contraction to the retraction device. At 514, the method may also provide for receiving the signal for compression at the retraction device. At 516, the method may also provide for processing the signal for compression at the retraction device. At 518, the method may also provide for contracting the expandable portion of the retraction device compared to the fixed portion, thereby causing a reduction of the opening.

Figure 6:
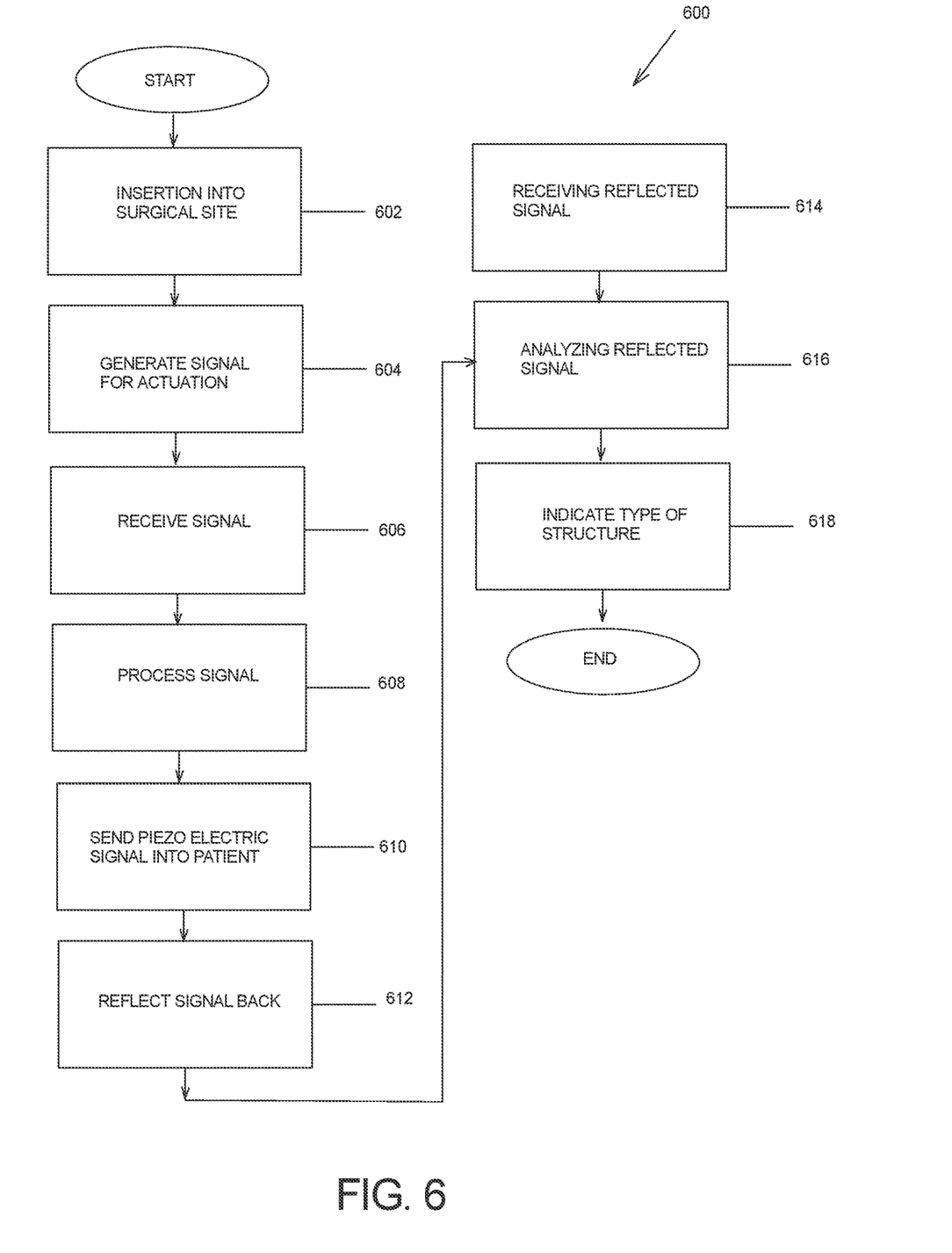
FIG. 6 is a method for identifying nerve structures during a spinal surgery using a multi-zone piezoelectric apparatus.

Referring to FIG. 6, a method 600 for identifying nerve structures during a spinal surgery using a multi-zone piezoelectric apparatus is illustrated. As will be understood, the apparatus disclosed above with reference to FIG. 3 may be used to accomplish this method 600. The method 600 may include, at 602, inserting a multi-zone piezoelectric apparatus into a surgical site. At 604, a signal for actuation of at least one piezoelectric component is generated. At 606, the signal for action is received at the multi-zone electric apparatus. At 608, the signal for action is processed by the multi-zone piezoelectric apparatus. At 610, at least one piezoelectric component of the piezoelectric apparatus is activated, sending a signal into a patient. At 612, the method further comprises reflecting the signal back to the apparatus. At 614, the method further comprises receiving the reflected signal by the apparatus. At 616, the method further comprises analyzing the reflected signal. At 618, the method comprises indicating a type of structure encountered by the signal. The indication may be a light or computer notification identifying a presence of a nerve, muscle and/or bone as non-limiting embodiments.

As will be understood, the varying densities of the bodily structures will reflect piezoelectric signals to a greater or lesser degree. Based upon the reflected signal, the analysis conducted in 616 may indicate the type of structure. During the method performed in relation to FIG. 6, illumination and/or video is obtained, aiding in the view of the surgeon. Video, piezoelectric analysis and pictures may be retained by a computing apparatus for archival purposes. In embodiments, azimuthal analysis of the nerve detecting apparatus may indicate to the surgeon what type of structure is being encountered. For example, a red light may illuminate on the apparatus if a nerve has been encountered. A blue light may illuminate if bone is encountered and a green light may illuminate if muscle is encountered. All of these indication lights may occur at the point of incision, thereby allowing the surgeon to concentrate at the point of surgery instead of looking elsewhere to view video.

In embodiments, a safety system may be included such that if a nerve is encountered, further progression of the surgery may be temporarily halted until an override command is provided by the surgeon, thereby limiting the amount of human error possible in such a surgery.

Embodiments may also allow for incorporation of the apparatus described in robotic surgical systems. Such robotic surgical systems may be autonomous or "remote" type surgical systems allowing the surgeon to accomplish surgery from a distant location.

As will be understood, aspects of the disclosure should not be limited to surgical procedures performed on humans. Surgical operations may be performed on animals, for example, providing a similar result. As will be understood, such use on animals with smaller bodies have several distinct advantages over conventional apparatus. Operations on smaller animals, where space is congested with various nerves and blood vessels, can derive benefit from such apparatus to minimize the amount of damage caused from surgery.

In one example embodiment, an apparatus for retraction is disclosed. The apparatus comprises a fixated portion and a movable portion, wherein the movable portion is configured to move relative to the fixated portion upon an actuation. The apparatus further configured with an actuator configured to receive a signal, process the received signal and perform an actuation to move the movable portion relative to the fixated portion.

In another embodiment, a method is described. The method comprises placing a retraction device within an opening, the retraction having both a fixed portion and an expandable portion. The method further comprises generating a signal for actuation of the retraction device. The method further comprises receiving the signal is received at the retraction device. The method further comprises processing the signal at the retraction device to determine when an actuation is to occur. The method further comprises actuating an actuator when the processing of the signal is determined that an actuation is to occur. The method further comprises moving the expandable portion through the actuator.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may be varied in many ways. Such variations are not to be regarded as a departure from the disclosure, and all such modifications are intended to be included within the scope of the disclosure.

In one example embodiment, a method is disclosed. The method comprises inserting a multi-zone piezoelectric apparatus into a surgical site and generating a signal for actuation of at least one piezoelectric component. The method further comprises receiving the signal for action at the multi-zone piezoelectric apparatus. The method further comprises processing the signal by the multi-zone piezoelectric apparatus. The method may further comprise activating at least one piezoelectric component of the piezoelectric apparatus. The method may further comprise reflecting the signal back to the apparatus from at least one structure. The method may also provide for receiving the reflected signal by the apparatus. The method may also provide for analyzing the reflected signal and indicating a type of structure encountered by the signal.

While embodiments have been described herein, those skilled in the art, having benefit of this disclosure, will appreciate that other embodiments are envisioned that do not depart from the inventive scope. Accordingly, the scope of the present claims or any subsequent claims shall not be unduly limited by the description of the embodiments described herein.

What is claimed is:

1. A method, comprising:
inserting a multi-zone piezoelectric apparatus into a surgical site;
generating an activation signal for actuation of at least one piezoelectric component;
receiving the activation signal for action at the multi-zone piezoelectric apparatus;
processing the activation signal by the multi-zone piezoelectric apparatus;
activating at least one piezoelectric component of the piezoelectric apparatus;
reflecting a return signal back to the apparatus from at least one structure;
receiving the return signal by the apparatus;
analyzing the return signal;
determining whether the return signal is indicative of a nerve, a bone or a muscle; and
displaying a first indicator when the determining is indicative of the nerve, a second indicator when the determining is indicative of the bone and a third indicator when the determining is indicative of the muscle, wherein the first, second and third indicators are different colors of light on the multi-zone piezoelectric apparatus.

2. The method of claim 1, further comprising halting a surgery if the return signal is indicative of a nerve until an override code is used.

3. The method of claim 1, wherein the surgical site is for a spinal surgical procedure.

4. The method of claim 1, wherein the displaying is on the multi-zone piezoelectric apparatus at the surgical site.

5. The method of claim 1, further comprising passing medical instruments through a tube of the multi-zone piezoelectric apparatus.

6. The method of claim 1, wherein the at least one piezoelectric component is at a tip of the multi-zone piezoelectric apparatus having an elongated shape.

7. The method of claim 1, wherein the at least one piezoelectric component is at a side of the multi-zone piezoelectric apparatus having an elongated shape.

8. The method of claim 1, wherein the at least one piezoelectric component includes a first piezoelectric component at a side of the multi-zone piezoelectric apparatus having an elongated shape and a second piezoelectric component at a tip of the multi-zone piezoelectric apparatus.

9. An apparatus for detecting type of body structure encountered in surgery, comprising:
   an elongated device for insertion into a surgical incision;
   a sensing section of the elongated device configured to detect the body structure when placed in proximity to the body structure by a surgeon using the elongated device; and
   a display located on the elongated device for displaying at the surgical incision a first indicator when the sensing section is proximate nerve, a second indicator when the sensing section is proximate bone and a third indicator when the sensing section is proximate muscle, wherein the first, second and third indicators are different colors of a light forming the display on the elongated device.

10. The apparatus of claim 9, wherein the sensing section includes a piezoelectric transducer and a sensor for detecting vibrational dynamics of the body structure activated by the piezoelectric transducer.

11. The apparatus of claim 9, wherein the sensing section includes a light source and reflected light sensor for optical determination of the type of body structure.

12. The apparatus of claim 9, wherein the sensing section includes a light source and reflected light sensor for optical determination of the type of body structure based on reference nerve, muscle and bone reflectance spectroscopy.

13. The apparatus of claim 9, wherein the elongated device is a tube configured to allow for passage of medical instruments through the elongated device.

14. The apparatus of claim 9, wherein the sensing section is at a tip of the elongated device.

15. The apparatus of claim 9, wherein the sensing section is at a side of the elongated device.

16. The apparatus of claim 9, wherein the sensing section is at both a tip and a side of the elongated device.

* * * * *

UNITED STATES PATENT AND TRADEMARK OFFICE
CERTIFICATE OF CORRECTION

| | | |
|---|---|---|
| PATENT NO. | : 11,974,735 B2 | Page 1 of 1 |
| APPLICATION NO. | : 17/945838 | |
| DATED | : May 7, 2024 | |
| INVENTOR(S) | : Rahman | |

It is certified that error appears in the above-identified patent and that said Letters Patent is hereby corrected as shown below:

On the Title Page

Item (73):
"Assignee: Ra'Kerry Rahman, Houston, TX (US)"
Should read:
"Assignee: Ra'Kerry Rahman MD PA, Houston, TX (US)"

Signed and Sealed this
Eighteenth Day of June, 2024

*Katherine Kelly Vidal*

Katherine Kelly Vidal
*Director of the United States Patent and Trademark Office*